US012751643B2

(12) United States Patent
Pacce

(10) Patent No.: US 12,751,643 B2
(45) Date of Patent: Oct. 6, 2026

(54) METHODS OF DISPLAYING VENTILATION DISTRIBUTION AND RELATED SYSTEMS AND DEVICES

(71) Applicant: Timpel Medical B.V., Eindhoven (NL)

(72) Inventor: Pedro Henrique Dalla Pacce, Sao Bernardo do Campo (BR)

(73) Assignee: Timpel Medical B.V., Eindhoven (NL)

( * ) Notice: Subject to any disclaimer, the term of this patent is extended or adjusted under 35 U.S.C. 154(b) by 1078 days.

(21) Appl. No.: 17/769,676

(22) PCT Filed: Oct. 16, 2020

(86) PCT No.: PCT/IB2020/059778
§ 371 (c)(1),
(2) Date: Apr. 15, 2022

(87) PCT Pub. No.: WO2021/074891
PCT Pub. Date: Apr. 22, 2021

(65) Prior Publication Data

US 2022/0378324 A1 Dec. 1, 2022

Related U.S. Application Data

(60) Provisional application No. 62/916,948, filed on Oct. 18, 2019.

(51) Int. Cl.

| | |
|---|---|
| ***A61B 5/0536*** | (2021.01) |
| ***A61B 5/091*** | (2006.01) |
| *A61B 5/00* | (2006.01) |

(52) U.S. Cl.
CPC ............ *A61B 5/091* (2013.01); *A61B 5/0536* (2013.01); *A61B 5/6823* (2013.01)

(58) Field of Classification Search
None
See application file for complete search history.

(56) References Cited

U.S. PATENT DOCUMENTS

| | | | | |
|---|---|---|---|---|
| 2007/0007973 A1* | 1/2007 | Matthiessen ......... | A61B 5/0536 324/692 |
| 2010/0069725 A1* | 3/2010 | Al-Ali .................. | A61B 5/7282 600/301 |

(Continued)

FOREIGN PATENT DOCUMENTS

| | | |
|---|---|---|
| EP | 2228009 A1 | 9/2010 |
| EP | 2407100 A1 | 1/2012 |

OTHER PUBLICATIONS

International Search Report for International Application No. PCT/IB2020/059778, mailed Mar. 1, 2021, 4 pages.

(Continued)

*Primary Examiner* — Adam J Eiseman
*Assistant Examiner* — Nelson Alexander Glover
(74) *Attorney, Agent, or Firm* — TraskBritt

(57) ABSTRACT

A system and related methods for displaying a ventilation distribution of a patient. The system may include a measuring system for measuring the ventilation distribution of the patient and a display device. The system may further include a controller operably coupled to the measuring system and the display device configured to cause the measuring system to measure the ventilation distribution of the patient at a time interval and plot an element representing the measured ventilation distribution of the patient within a Cartesian coordinate system of a graphical user interface of the display device. The element may be plotted with a higher intensity relative to other elements representing previously measured ventilation distributions of the patient.

24 Claims, 6 Drawing Sheets

(56) References Cited

U.S. PATENT DOCUMENTS

| | | | | |
|---|---|---|---|---|
| 2012/0016254 | A1* | 1/2012 | Masuo | A61B 5/053 600/547 |
| 2015/0216443 | A1* | 8/2015 | Baier-Lowenstein | A61M 5/007 600/431 |
| 2015/0379706 | A1* | 12/2015 | Leonhardt | G06T 11/003 382/131 |
| 2016/0119210 | A1* | 4/2016 | Koehler | A61B 5/7282 370/245 |
| 2019/0246949 | A1 | 8/2019 | Holzhacker | |
| 2019/0328268 | A1* | 10/2019 | Woo | A61B 5/0205 |
| 2020/0016352 | A1* | 1/2020 | Stender | A61B 5/6823 |
| 2022/0160249 | A1* | 5/2022 | Zhang | G06T 15/00 |

OTHER PUBLICATIONS

International Written Opinion for International Application No. PCT/IB2020/059778, mailed Mar. 1, 2021, 7 pages.
Laufer et al., “Lung mechanics—airway resistance in the dynamic elastance model”, Health Technol. (2017) 7:61-70.
Bikker et al., “Electrical impedance tomography measured at two thoracic levels can visualize the ventilation distribution changes at the bedside during a decremental positive end-expiratory lung pressure trial”, Critical Care 2011, 15:R193, 8 pages.
Dmytrowich et al., “Mechanical ventilation guided by electrical impedance tomography in pediatric acute respiratory distress syndrome”, J Clin Monit Comput (2018) 32:503-507.

* cited by examiner

METHODS OF DISPLAYING VENTILATION DISTRIBUTION AND RELATED SYSTEMS AND DEVICES

CROSS-REFERENCE TO RELATED APPLICATIONS

This application is a national phase entry under 35 U.S.C. § 371 of International Patent Application PCT/IB2020/059778, filed Oct. 16, 2020, designating the United States of America and published as International Patent Publication WO 2021/074891 A4 on Apr. 22, 2021, which claims the benefit under Article 8 of the Patent Cooperation Treaty to U.S. Patent Application Ser. No. 62/916,948, filed Oct. 18, 2019.

TECHNICAL FIELD

Embodiments of the present disclosure generally relate to medical support systems. In particular, embodiments of the present disclosure relate to methods of determining and displaying ventilation distribution and related systems and devices.

BACKGROUND

Ventilation distribution provides a measurement that physicians can use to determine how a patient's lungs are directing and processing air being breathed by the patient. A physician can use ventilation distribution to diagnose illnesses and/or conditions that affect the distribution of air within the lungs, such as pneumothorax, lung disease, pneumonia, acute respiratory distress syndrome, selective intubation, etc. Ventilation distribution may be measured through multiple techniques such as Computed Tomography Scans (CT), electrical impedance tomography (EIT), ultrasonic flow meters, tracer gas, etc.

Ventilation distribution is typically represented as directional percentages. For example, the ventilation distribution may be represented as a percent left or right and a percent anterior or posterior. Conventionally, ventilation distribution is displayed as a number representing the distribution ratio or as a graph representing the distribution ratio over time.

BRIEF SUMMARY

Embodiments of the present disclosure may include a method of displaying a ventilation distribution for a patient. The method may include measuring a first ventilation distribution for the patient at a first time. The method may further include plotting the first ventilation distribution within a graphical user interface of a display. The method may also include measuring a second ventilation distribution for the patient at a second time. The method may further include plotting the second ventilation distribution within the graphical user interface of the display. The method may also include in response to plotting the second ventilation distribution, adjusting a visual property of the first ventilation distribution. The adjusted visual property of the first ventilation distribution may visually distinguish the first ventilation distribution from the second ventilation distribution.

Another embodiment of the present disclosure may include a system for displaying a ventilation distribution of a patient. The system may include a measuring system for measuring the ventilation distribution of the patient. The system may also include a display device. The system may further include a controller operably coupled to the measuring system and the display device. The controller may include at least one processor, and at least one non-transitory computer readable storage medium storing instructions thereon. When executed by the at least one processor, the instruction may cause the at least one processor to cause the measuring system to measure the ventilation distribution of the patient at a time interval. The instructions may further cause the at least one processor to plot an element representing the measured ventilation distribution of the patient within a Cartesian coordinate system of a graphical user interface of the display device. The element may be plotted with a higher intensity relative to other elements representing previously measured ventilation distributions of the patient.

Another embodiment of the present disclosure may include a system for displaying a ventilation distribution of a patient. The system may include at least one processor; and at least one non-transitory computer readable storage medium. The storage medium may store instructions thereon that, when executed by the at least one processor, may cause the at least one processor to repeatedly receive a ventilation distribution measurement of the patient. The instructions may further cause the at least one processor to repeatedly display the ventilation distribution measurement of the patient. The instructions may also cause the at least one processor to repeatedly adjust a visual intensity of one or more earlier displayed ventilation distribution measurement.

DETAILED DESCRIPTION

Figure 1:
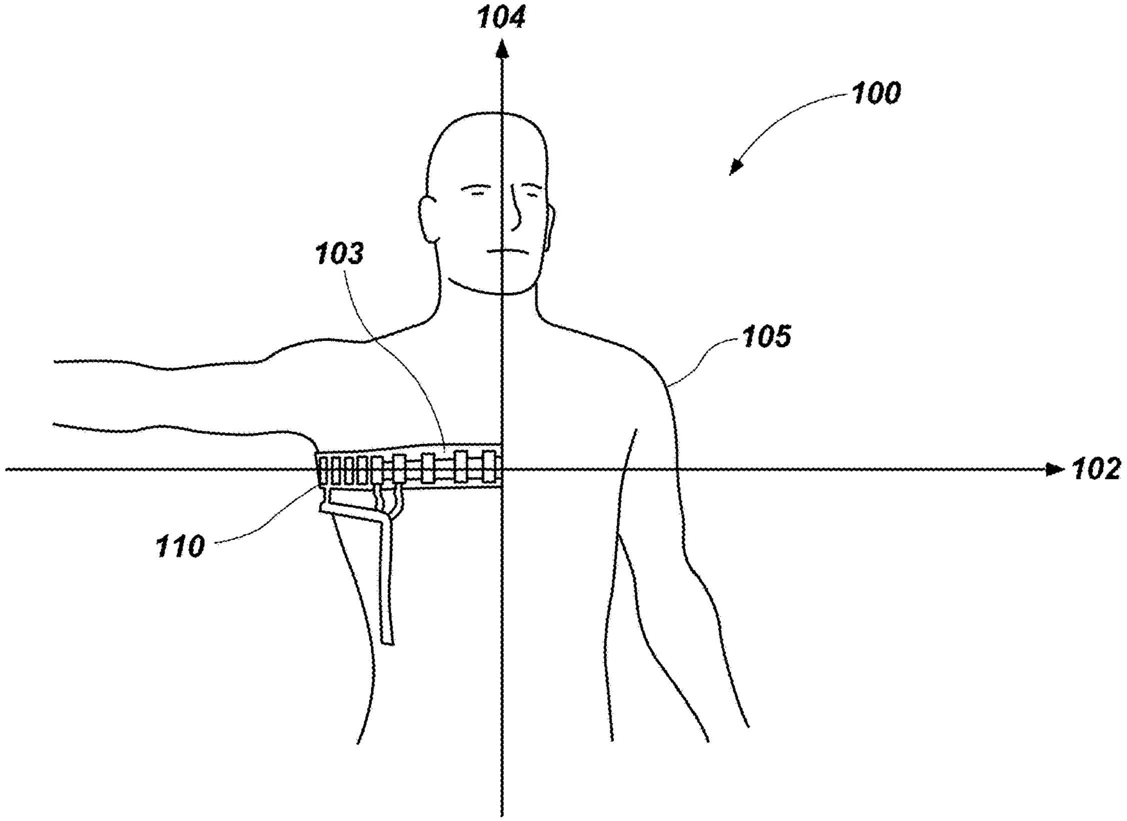
FIG. 1 is a schematic diagram of a portion of an EIT system showing a plurality of electrodes positioned around a region of interest of a patient according to one or more embodiments of the present disclosure.

The illustrations presented herein are not meant to be actual views of any particular system, method, or component thereof, but are merely idealized representations employed to describe illustrative embodiments. The drawings are not necessarily to scale.

As used herein, the term “substantially” in reference to a given parameter means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, at least about 99% met, or even at least about 100% met.

As used herein, relational terms, such as “first,” “second,” “top,” “bottom,” “upper,” “lower,” “right,” “left,” etc., are generally used for clarity and convenience in understanding the disclosure and accompanying drawings and do not connote or depend on any specific preference, orientation, or order, except where the context clearly indicates otherwise.

As used herein, the term “and/or” means and includes any and all combinations of one or more of the associated listed items.

As used herein, the terms “vertical” and “horizontal” refer to the orientations as depicted in the figures.

Ventilation distribution provides a measurement that physicians can use to determine how a patient’s lungs are directing and processing air being breathed by the patient. While, a physician may use ventilation distribution to diagnose illnesses and/or conditions that affect the distribution of air within the lungs, such as pneumothorax, lung disease, pneumonia, acute respiratory distress syndrome, selective intubation, etc., changes in the ventilation distribution over time may enable the physician to evaluate one or more of the effectiveness of a treatment being administered, the recovery of the patient, a speed of the patient’s recovery, the development of a condition, etc. The changes in the ventilation distribution may enable the physician to adjust the treatment earlier when a first treatment is not effectively treating the condition or illness. For example, if the original diagnosis is incorrect the changes in ventilation distribution or lack thereof may enable the physician to identify and/or correct the diagnosis. In some embodiments, a medication or ventilatory parameters may be adjusted when the changes in ventilation distribution are not progressing in the expected manner. For example, the physician may adjust a dosage or change the type of medication, such as switching to a different antibiotic, based on changes in ventilation distribution or lack thereof.

Ventilation distribution is typically represented as directional percentages. For example, the ventilation distribution may be represented as a side-to-side percentage, such as a left distribution percentage or a right distribution percentage and a front-to-back percentage such as, an anterior distribution percentage or a posterior distribution percentage. Conventionally, ventilation distribution is displayed as a number representing the distribution ratio or as a graph representing the distribution ratio over time. A graph of the distribution ratio over time may be difficult for a physician to evaluate quickly requiring the physician to determine if the ratio change represents a beneficial change or a negative change in ventilation distribution. Embodiments of the present disclosure include a system for displaying a representation of a ventilation distribution that may enable a physician to quickly evaluate changes in the ventilation distribution over time in order to better diagnose and treat pulmonary conditions and/or diseases.

Embodiments of the disclosure may include an EIT device configured to measure a ventilation distribution of a patient. In some embodiments, the ventilation distribution of the patient may be measured using other known processes and/or devices such as ultrasonic flow metering, CT scans, Mill, tracer gas, etc. The EIT or other device may measure a tidal impedance or lung impedance. The ventilation distribution may then be calculated using the tidal impedance in each region of the patient’s lungs.

EIT is an imaging technique involving the positioning of electrodes via an electrode belt placed around a region of a patient’s body (e.g., around the patient’s chest for imaging of a lung), injecting electrical excitation signals through a pair of electrodes, and measuring the induced response signals detected by the other electrodes of the electrode belt. As a result, the EIT system may generate an image based on the voltage measurements indicating estimated impedance values. In contrast with other imaging techniques, EIT is non-invasive and does not have certain exposure risks that might limit the number and frequency of monitoring actions (e.g., as with techniques such as X-rays). As a result, EIT is suitable for continuously monitoring the condition of the patient, with particular application to monitoring the patient’s lungs as the measurements may be used to determine respiratory and hemodynamic parameters of the patient and monitor a real-time two-dimensional image.

FIG. 1 is a schematic diagram of a portion of an EIT system 100 showing a plurality of electrodes 110 positioned around a region of interest (e.g., thorax) of a patient 105. The electrodes 110 of conventional EIT systems 100 are typically physically held in place by an electrode belt 103. The placement of the electrodes 110 is typically transverse to the cranial caudal axis 104 of the patient. Although the electrodes 110 are shown in FIG. 1 as being placed only partially around the patient 105, electrodes 110 may by placed around the entire patient 105 depending on the specific region of interest available or desired for measurement. The electrodes 110 may be coupled to a computing system (not shown) configured to control the operation of the electrodes 110 and perform reconstruction of the EIT image.

Figure 2:
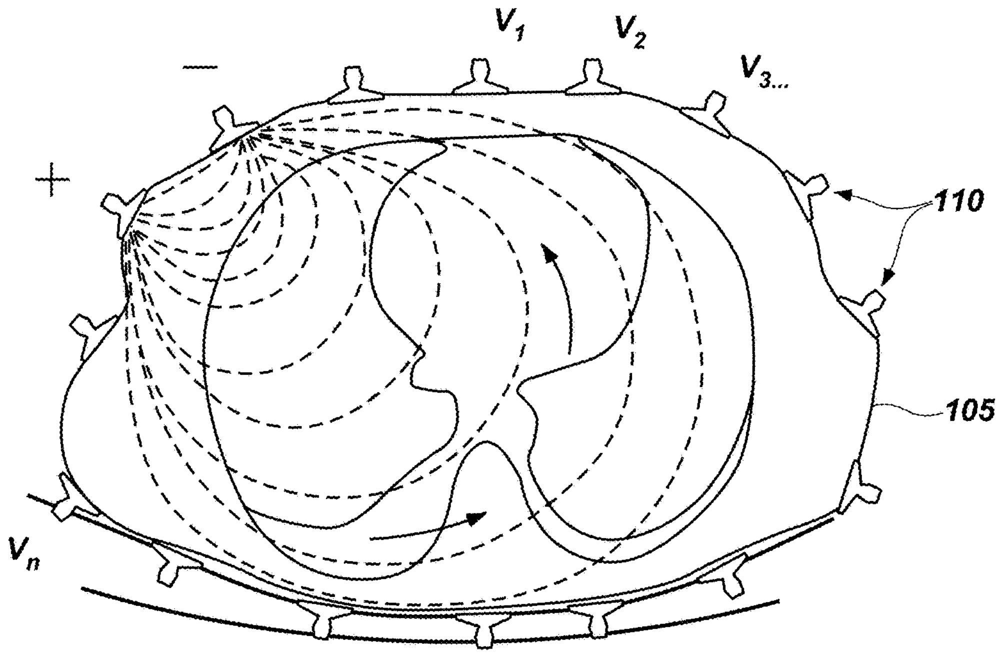
FIG. 2 is a schematic diagram showing a cross-section of the thorax of the patient along the plane of the electrodes according to one or more embodiments of the present disclosure.

FIG. 2 is a schematic diagram showing a cross-section of the thorax of the patient 105 along the plane of the electrodes. A voltage may be applied to a pair of electrodes 110 (shown by the electrodes having a + and − symbol) to inject an excitation current into the patient between an electrode pair. As a result, voltages (e.g., V1, V2, V3 . . . Vn) may be detected by the other electrodes and measured by the EIT system 100. Current injection may be performed for a measurement cycle according to a circular pattern using different electrode pairs to generate the excitation current.

Figure 3:
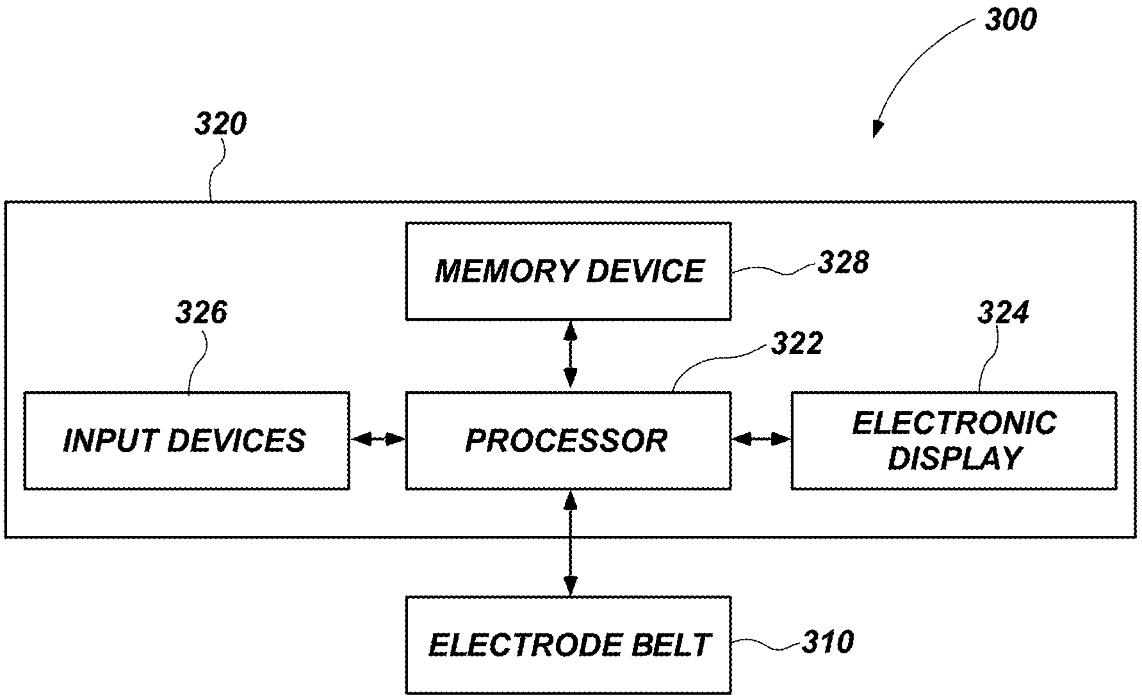
FIG. 3 is a schematic block diagram of an EIT system according to an embodiment of the disclosure.

FIG. 3 is a schematic block diagram of an EIT system 300 according to an embodiment of the disclosure. The EIT system 300 may include an electrode belt 310 operably coupled with a data processing system 320. The electrode belt 310 and the data processing system 320 may be coupled together via a wired connection (e.g., cables) and/or may have communication modules to communicate wirelessly with each other. The data processing system 320 may include a processor 322 operably coupled with an electronic display 324, input devices 326, and a memory device 328. The electronic display 324 may be constructed with the data processing system 320 into a singular form factor for an EIT device coupled with the electrode belt 310. In some embodiments, the electronic display 324 and the data processing system 320 may be separate units of the EIT device coupled with the electrode belt 310. In yet other embodiments, an EIT system 300 may be integrated within another host system configured to perform additional medical measurements and/or procedures, in which the electrode belt 310 may couple to a port of the host system already having its own input devices, memory devices, and electronic display. As such, the host system may have the EIT processing software installed therein. Such software may be built into the host system prior to field use or updated after installation.

The processor 322 may coordinate the communication between the various devices as well as execute instructions stored in computer-readable media of the memory device 328 to direct current excitation, data acquisition, data analysis, and/or image reconstruction. As an example, the memory device 328 may include a library of finite element meshes used by the processor 322 to model the patient's body in the region of interest for performing image reconstruction. Input devices 326 may include devices such as a keyboard, touch screen interface, computer mouse, remote control, mobile devices, or other devices that are configured to receive information that may be used by the processor 322 to receive inputs from an operator of the EIT system 300. Thus, for a touch screen interface the electronic display 324 and the input devices 326 receiving user input may be integrated within the same device. The electronic display 324 may be configured to receive the data and output the EIT image reconstructed by the processor for the operator to view. Additional data (e.g., numeric data, graphs, trend information, and other information deemed useful for the operator) may also be generated by the processor 322 from the measured EIT data alone, or in combination with other non-EIT data according to other equipment coupled thereto. Such additional data may be displayed on the electronic display 324.

The EIT system 300 may include components that are not shown in the figures, but may also be included to facilitate communication and/or current excitation with the electrode belt 310 as would be understood by one of ordinary skill in the art, such as including one or more analog to digital converter, signal treatment circuits, demodulation circuits, power sources, etc.

Figure 4:
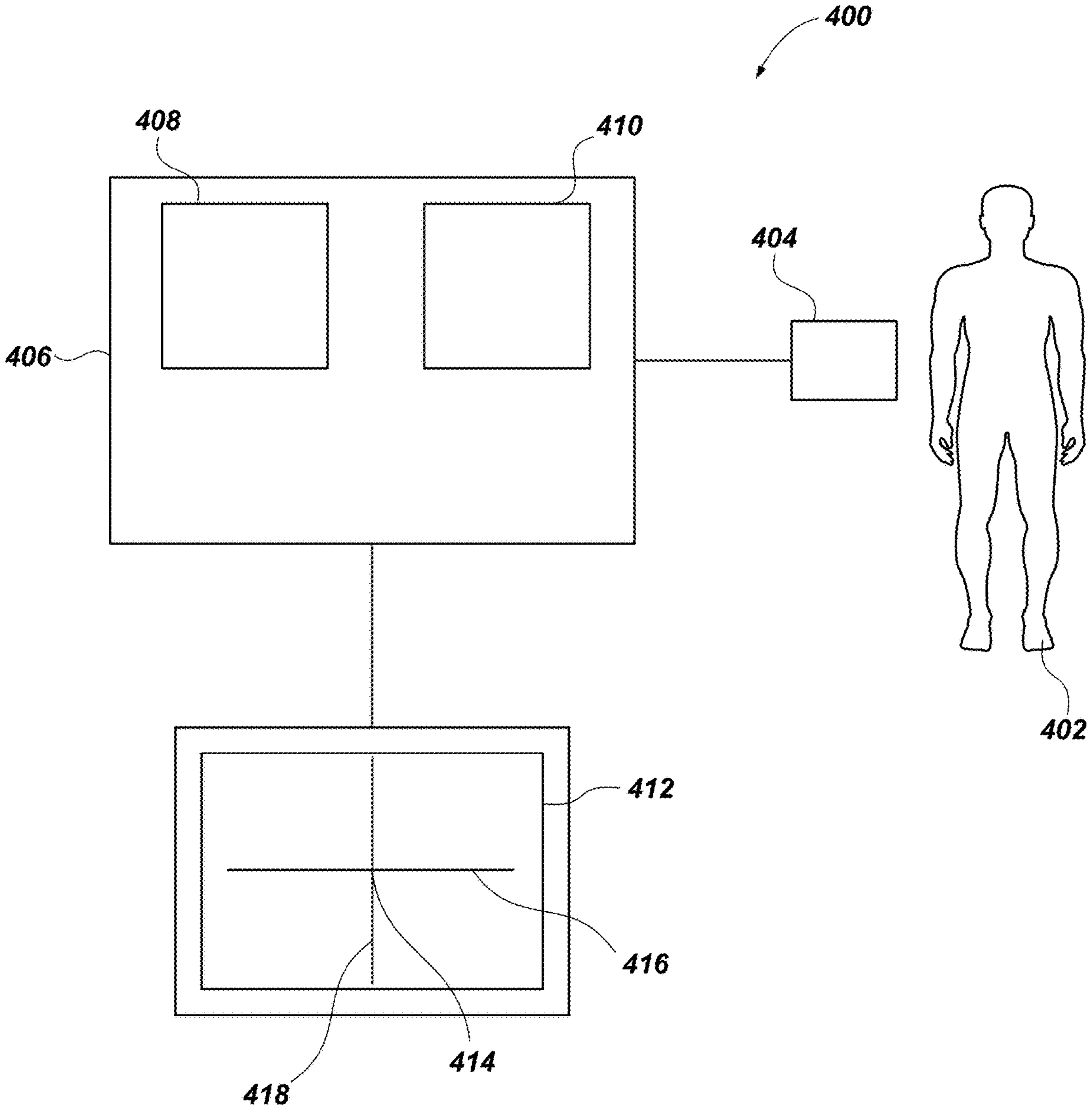
FIG. 4 is a schematic block diagram of a system for communicating a ventilation distribution measurement from a patient according to an embodiment of the disclosure.

FIG. 4 illustrates a system 400 for communicating (e.g., generating and displaying) a measured ventilation distribution of a patient 402 to a physician. The system 400 may include a measuring system 404 configured to measure a ventilation distribution of a patient 402. The measuring system 404 may include an EIT system such as the EIT system 300 described above. In some embodiments, the measuring system 404 may include ultrasonic flow metering system, magnetic resonance imaging (MRI) system, Computed Tomography (CT) system, tracer gas system, and/or other known methods or devices for measuring a ventilation distribution of the patient 402. The measuring system 404 may be configured to measure the ventilation distribution of the patient 402 at intervals. For example, the measuring system 404 may be configured to measure the ventilation distribution of the patient 402 at each breath of the patient 402, every other breath of the patient 402, every third breath of the patient 402, etc. In some embodiments, the measuring system 404 may be configured to measure the ventilation distribution of the patient 402 at specific time intervals, such as, once a minute, once every thirty seconds, once every two minutes, etc.

The measuring system 404 may be operably coupled to a controller 406. The controller 406 may include a processor 408 and a memory 410. The processor 408 may be configured to receive the ventilation distribution measurements (e.g., data related to the ventilation distribution measurements) from the measuring system 404. In some embodiments, the processor 408 may store the ventilation distribution measurements in the memory 410 (e.g., database). The processor 408 may also generate a visual representation of the ventilation distribution measurements and may cause the visual representation to be displayed on a display 412 for viewing by a physician. For example, the controller 406 may generate one or more graphical user interfaces ("GUIs") showing the ventilation distribution measurements and may cause the GUIs to be displayed on the display 412. A GUI typically includes one or more display regions and active/activatable regions. As used in this disclosure, a display region is a region of a GUI, which displays information to a user. An activatable region is a region of a GUI, such as a button, slider, or a menu, which allows the user to take some action with respect to the GUI (e.g., if manipulated). Some display regions are also activatable regions in that the activatable regions display information and enable some action that may be taken by a user. In a contact-sensitive GUI, contacting a contact-sensitive area associated with an activatable region may activate that region (e.g., selecting a GUI button). Activatable regions may be displayed as GUI elements/objects, for example, buttons, sliders, selectable panes, menus, etc., all of various shapes and sizes. In particular, the components (e.g., the activatable regions of the GUI) may allow a user to interact with a collection of display elements for a variety of purposes. In particular, FIGS. 5-7 and the description that follows illustrate various example embodiments of the user interfaces and features that are in accordance with one or more embodiments of the present disclosure.

In some embodiments, the display 412 may be coupled directly to the controller 406. In some embodiments, the display 412 may be coupled to the controller 406 through a network (e.g., a wireless network). For example, the processor 408 may transmit data packets including the GUIs and visual representations of the ventilation distribution measurements to a separate computer or controller to be processed, stored, displayed, or recorded. In some embodiments, the separate computer may include an additional display for displaying the GUIs and visual representations of the ventilation distribution measurements for viewing by the physician.

In some embodiments, the generated GUIs and visual representations and/or the display 412 itself may include a Cartesian coordinate 414 configured to display the ventilation distribution measurements to the physician in a clear manner. For example, the Cartesian coordinate 414 may include at least two axes. The axes may include a horizontal axis 416 and a vertical axis 418. In some embodiments, the horizontal axis 416 may represent a side-to-side distribution, such as right distribution percent or left distribution percent. In some embodiments, the vertical axis 418 may represent the front-to-back distribution, such as anterior distribution percent or posterior distribution percent.

The system 400 may cause all of the ventilation distribution measurements from the measuring system 404 to be displayed via the display 412 at the same time. A visual property of elements representing each measurement (each measurement at each interval) may be adjusted such that the physician can differentiate between the different ventilation distribution measurements (e.g., elements representing the different ventilation distribution measurements) of the patient 402. For example, an intensity such as the intensity of the color, brightness, or contrast of the elements (i.e., data points) with in the GUIs and visual representation may be varied based on the time stamp of each data point such that more recent ventilation distribution measurements have a higher intensity than older ventilation distribution measurements. The physician may be able to compare more recent ventilation distribution measurements with the older ventilation distribution measurements on the same display to quickly evaluate any changes in the ventilation distribution of the patient 402. The change in intensity and position of measurements between measurements also provides information as to the speed as relatively large changes in distribution will be represented as relatively large changes in position within the Cartesian coordinate 414.

Figure 5:
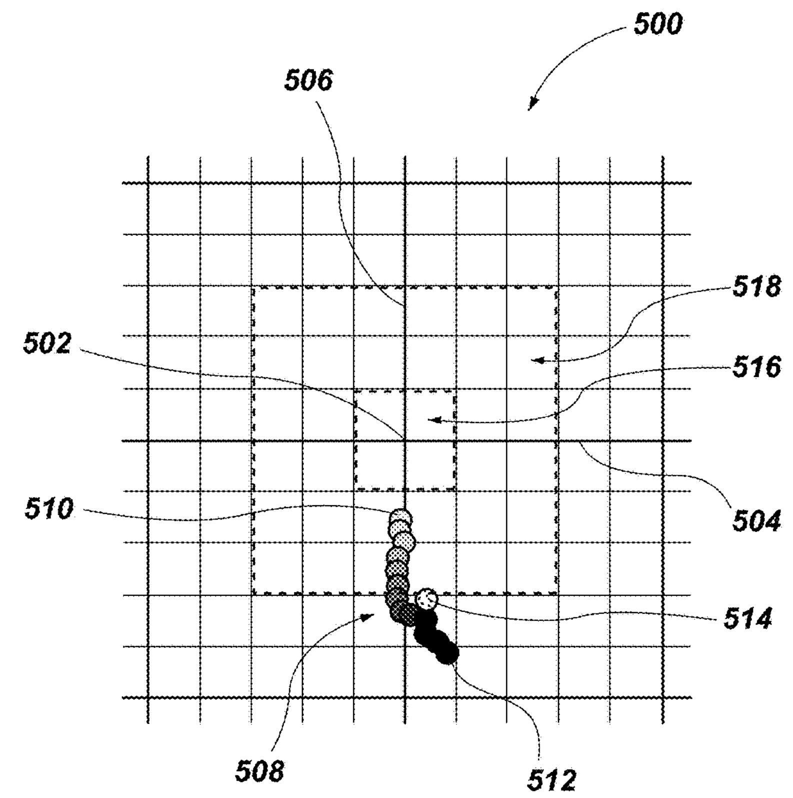
FIG. 5 is an example of a display of a ventilation distribution of a patient according to an embodiment of the present disclosure.

FIG. 5 illustrates an example of a ventilation distribution GUI plot 500 according to an embodiment of the present disclosure. The ventilation distribution GUI plot 500 may include a Cartesian coordinate 502. The Cartesian coordinate 502 may include a horizontal axis 504 and a vertical axis 506. The horizontal axis 504 may represent a side-to-side distribution, such as right distribution percent or left distribution percent. In some embodiments, the vertical axis 506 may represent the front-to-back distribution, such as anterior distribution percent or posterior distribution percent. In some embodiments, an intersection point between the horizontal axis 504 and the vertical axis 506 may represent a central point within a patient, such that ventilation distribution measurements plotted on a left side of the vertical axis 506 may represent a ventilation distribution biased in the left lung of the patient and ventilation distribution measurements plotted on a right side of the vertical axis 506 may represent a ventilation distribution biased in the right lung. Likewise, ventilation distribution measurements plotted above the horizontal axis 504 may represent a ventilation distribution biased in an anterior portion of the lungs and ventilation distribution measurements plotted below the horizontal axis 504 may represent a ventilation distribution biased in a posterior portion of the lungs.

The ventilation distribution measurements may be plotted on the ventilation distribution GUI plot 500 as data points 508. The data points 508 may represent multiple ventilation distribution measurements over a time period. Visual (e.g., display) properties of each of the data points 508 may be adjusted to indicate an age of the ventilation distribution measurement represented by the respective data point 508 relative to other data points 508 depicted within ventilation distribution GUI plot 500. For example, an older data points 510 may be presented in a lighter color, lighter shade, less contrast with the background, etc. Older data points 510 are visible but are also less intense than a more recent data points 512. Conversely, the more recent data points 512 may be presented in a darker color, darker shade, more contrast with the background, etc. More recent data points 512 may be more intense than the older data points 510. In some embodiments, a most recent data point 514 may be presented in a manner that emphasizes the most recent data point 514 over all of the other data points 508. For example, the most recent data point 514 may be presented in a different color than the surrounding data points 508 as illustrated in FIG. 5. In some embodiments, the most recent data point 514 may be highlighted or outlined with a bright color such as red or yellow.

Plotting a collection of data points 508 and distinguishing between the older data points 510 and the more recent data points 512 within the collection of data points 508 may enable a physician to easily evaluate changes in the ventilation distribution of the patient. For example, FIG. 5 illustrates that the ventilation distribution began at a position substantially along the vertical axis 506 and slightly below the horizontal axis 504 as illustrated by the older data points 510. Therefore, the older ventilation distribution measurements indicates that the ventilation distribution was substantially even between the right lung and left lung and distributed slightly to the posterior of both lungs. As the measurements progress, the ventilation distribution progresses farther into the posterior portion of the lungs and is biased into the right lung.

The ventilation distribution GUI plot 500 may enable the physician to quickly evaluate a treatment being used on the patient or a developing condition of the patient through the changes in the ventilation distribution illustrated by the data points 508.

In some embodiments, the ventilation distribution GUI plot 500 may further include emphasized target regions on the Cartesian coordinate 502. For example, the Cartesian coordinate 502 may include a desired region 516 and an acceptable region 518 emphasized on the Cartesian coordinate 502. The desired region 516 and acceptable region 518 may enable a physician to observe when the patient's ventilation distribution is acceptable and when the ventilation distribution indicates that corrective measures are required. Furthermore, as the ventilation distribution progresses toward a border of the acceptable region 518, the progression may be quickly and easily recognized by the physician enabling the physician to apply corrective measures before the ventilation distribution enters an at risk region, which may minimize the amount of time the ventilation distribution is in the at risk region before the corrective measure can take affect and the condition is rectified.

Figure 6:
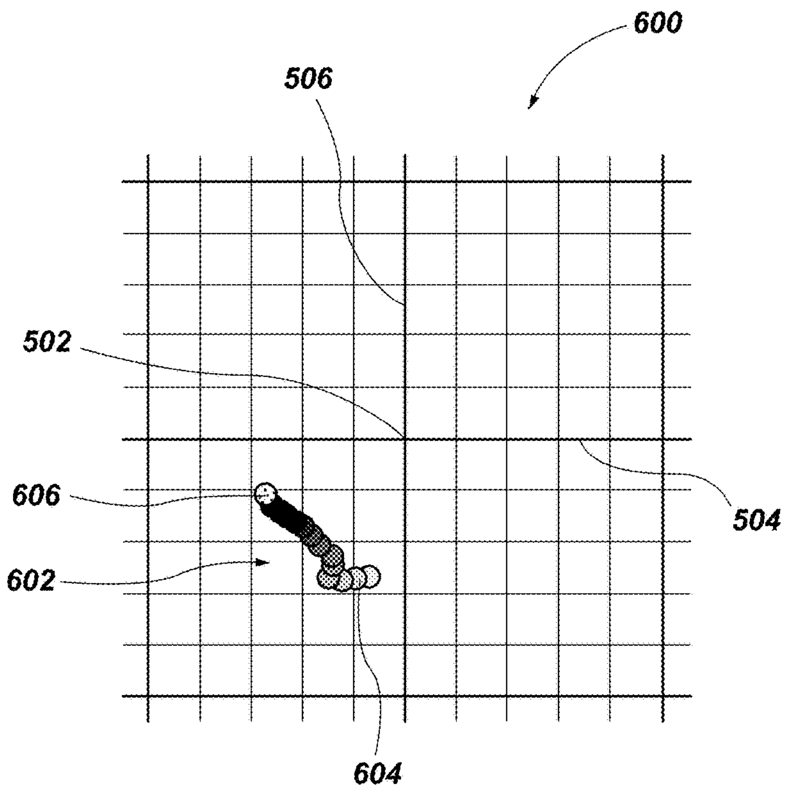
FIG. 6 is an example of a display of a ventilation distribution of a patient according to an embodiment of the present disclosure.

FIG. 6 illustrates another ventilation distribution GUI plot 600 according to an embodiment of the present disclosure. The ventilation distribution GUI plot 600 includes the Cartesian coordinate 502 having a horizontal axis 504 and a vertical axis 506. In some embodiments, the data points 602 plotted on the Cartesian coordinate 502 of the ventilation distribution GUI plot 600 may illustrate a developing condition such as a pneumothorax. In some embodiments, the data points 602 plotted on the Cartesian coordinate 502 of the ventilation distribution GUI plot 600 may illustrate a failing treatment.

The data points 602 illustrate a progression of the ventilation distribution of the patient where the older data points 604 are near the vertical axis 506 illustrating a relatively even ventilation distribution between the two lungs and the more recent data points 606 are heavily biased to a left lung illustrating a left ventilation distribution. A diminished capacity or effectiveness of the right lung may cause the ventilation distribution to bias largely to the left lung due to the diminished capacity or effectiveness of the right lung.

Therefore, the ventilation distribution GUI plot 600 may enable a physician to at the very least deduce that there is a problem with the right lung. The ventilation distribution GUI plot 600 may enable a skilled physician to eliminate some conditions based on a speed of the progression of the ventilation distribution to the left side. For example, the older data points 604 are concentrated near the vertical axis 506 whereas the more recent data points 606 rapidly progress from the area near the vertical axis 506 to the left side of the Cartesian coordinate 502 indicating that the condition developed quickly. Some physicians may even be able to fully diagnose a condition of the patient solely from the information provided by the progression of the ventilation distribution.

Figure 7:
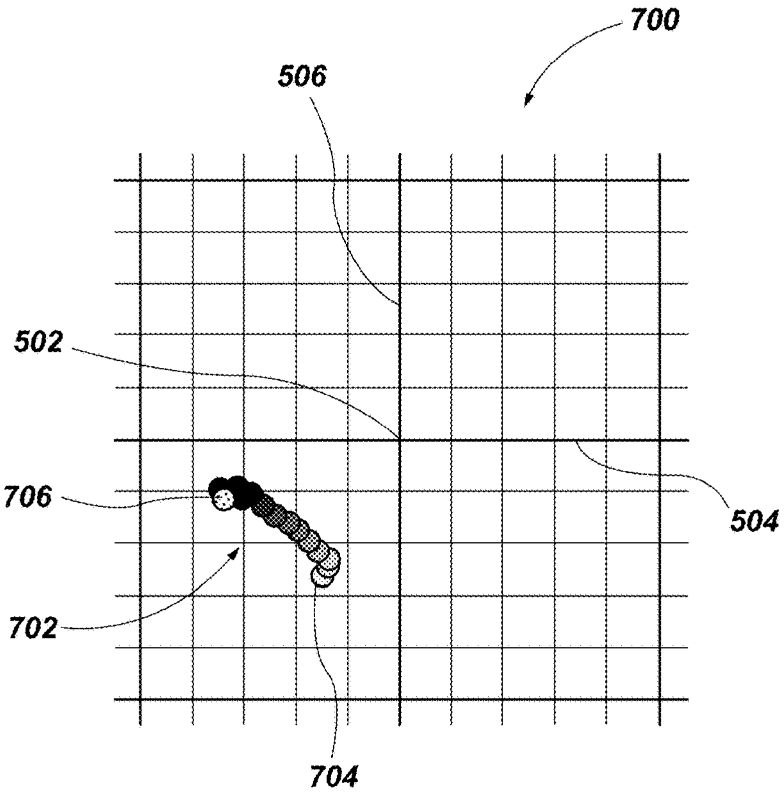
FIG. 7 is an example of a display of a ventilation distribution of a patient according to an embodiment of the present disclosure.

FIG. 7 illustrates another ventilation distribution GUI plot 700 according to an embodiment of the present disclosure. The ventilation distribution GUI plot 700 includes the Cartesian coordinate 502 having a horizontal axis 504 and a vertical axis 506. The data points 702 plotted on the Cartesian coordinate 502 of the ventilation distribution GUI plot 700 may illustrate a developing condition such as a pneumothorax. In other embodiments, the data points 702 plotted on the Cartesian coordinate 502 of the ventilation distribution GUI plot 700 may illustrate a treatment.

The data points 702 illustrate a progression of the ventilation distribution of the patient where the older data points 704 are near the vertical axis 506 illustrating a relatively even ventilation distribution between the two lungs and the more recent data points 706 are heavily biased to a left lung illustrating a left ventilation distribution. A diminished capacity or effectiveness of the right lung may cause the ventilation distribution to bias largely to the left lung due to the diminished capacity or effectiveness of the right lung.

In some embodiments, a physician may begin treating a condition or disease detected in the lungs. The physician may have an initial goal of halting the progression of the condition. For example, the ventilation distribution GUI plot 700 may illustrate that the condition developed rapidly as illustrated by the older data points 704 that rapidly progress from an area near the vertical axis 506 to a region largely biased to the left side of the Cartesian coordinate 502. The more recent data points 706 illustrate that the progression to the left side of the Cartesian coordinate 502 was substantially halted as the more recent data points 706 are concentrated in a small area. Thus, the data points 702 may illustrate that a treatment intended to halt the progression of the developing condition was substantially successful.

In another case, the treatment administered by the physician may be intended to correct the condition and return the ventilation distribution to a more even distribution near the vertical axis 506. In this case, the ventilation distribution GUI plot 700 may enable the physician to evaluate the effectiveness of the treatment. Because the more recent data points 706 are concentrated in the region on the left side of the Cartesian coordinate 502, the physician may determine that the treatment being administered is ineffective and enable the physician to quickly move to a different method of treatment.

Figure 8:
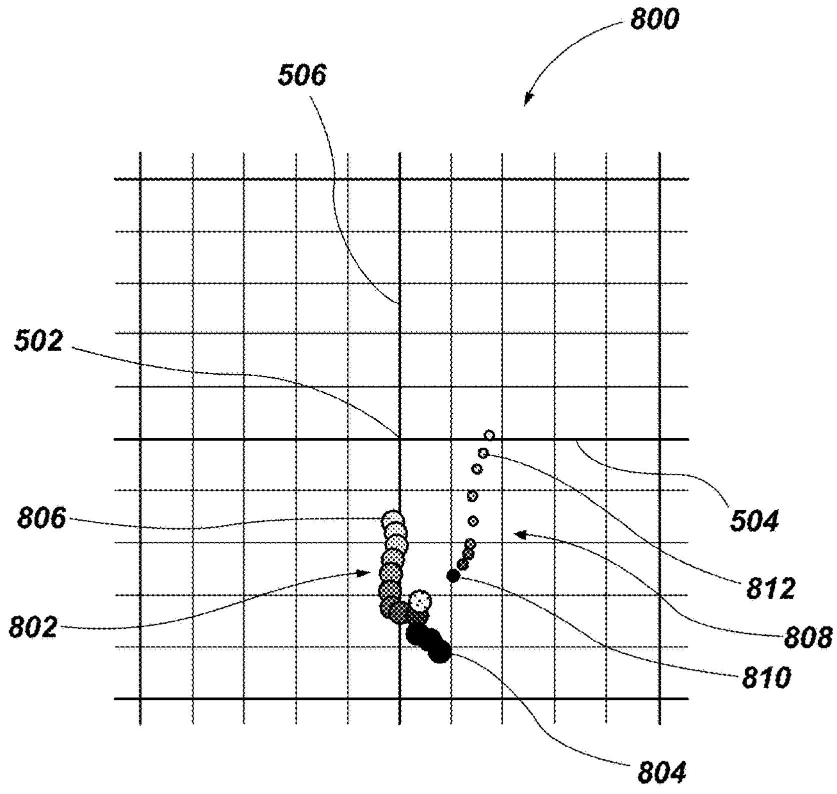
FIG. 8 is an example of a display of a ventilation distribution of a patient according to an embodiment of the present disclosure.

FIG. 8 illustrates another ventilation distribution GUI plot 800 according to one or more embodiments of the present disclosure. The ventilation distribution GUI plot 800 includes the Cartesian coordinate 502 having a horizontal axis 504 and a vertical axis 506. The ventilation distribution GUI plot 800 may include ventilation distribution data points 802 plotted on the Cartesian coordinate 502. As discussed above, the ventilation distribution data points 802 may include more recent ventilation distribution data points 804 plotted at a higher intensity than older ventilation distribution data points 806.

In some embodiments, the ventilation distribution GUI plot 800 may further include perfusion data points 808 plotted on the Cartesian coordinate 502. The perfusion data points 808 may correspond to a perfusion distribution within the lungs. The perfusion distribution may illustrate a distribution of blood cells within the lungs whereas the ventilation distribution may illustrate the distribution of air or oxygen within the lungs. Comparing perfusion distribution and ventilation distribution is commonly referred to as V/Q mapping. The perfusion distribution may be obtained and determine via conventional manners and methods.

The perfusion distribution may be plotted in a similar manner to the ventilation distribution. For example, the perfusion data points 808 may be plotted with more recent perfusion data points 810 having a higher intensity than older perfusion data points 812. In some embodiments, the ventilation distribution data points 802 and the perfusion data points 808 may be plotted in different colors or color gradients such that a viewer may easily distinguish between the ventilation distribution data points 802 and the perfusion data points 808.

As the patients ventilation distribution reaches a steady state (e.g., the ventilation distribution remains substantially the same for a period of time) the perfusion distribution may approach the ventilation distribution such that the ventilation distribution and the perfusion distribution are substantially the same. A plot illustrating both the ventilation distribution data points 802 and the perfusion data points 808 may enable a physician to easily see if a patient's ventilation distribution and perfusion distribution are approaching the same value as expected and desired. This may enable a physician to diagnose a problem or verify that a treatment is successfully treating a previous condition.

Figure 9:
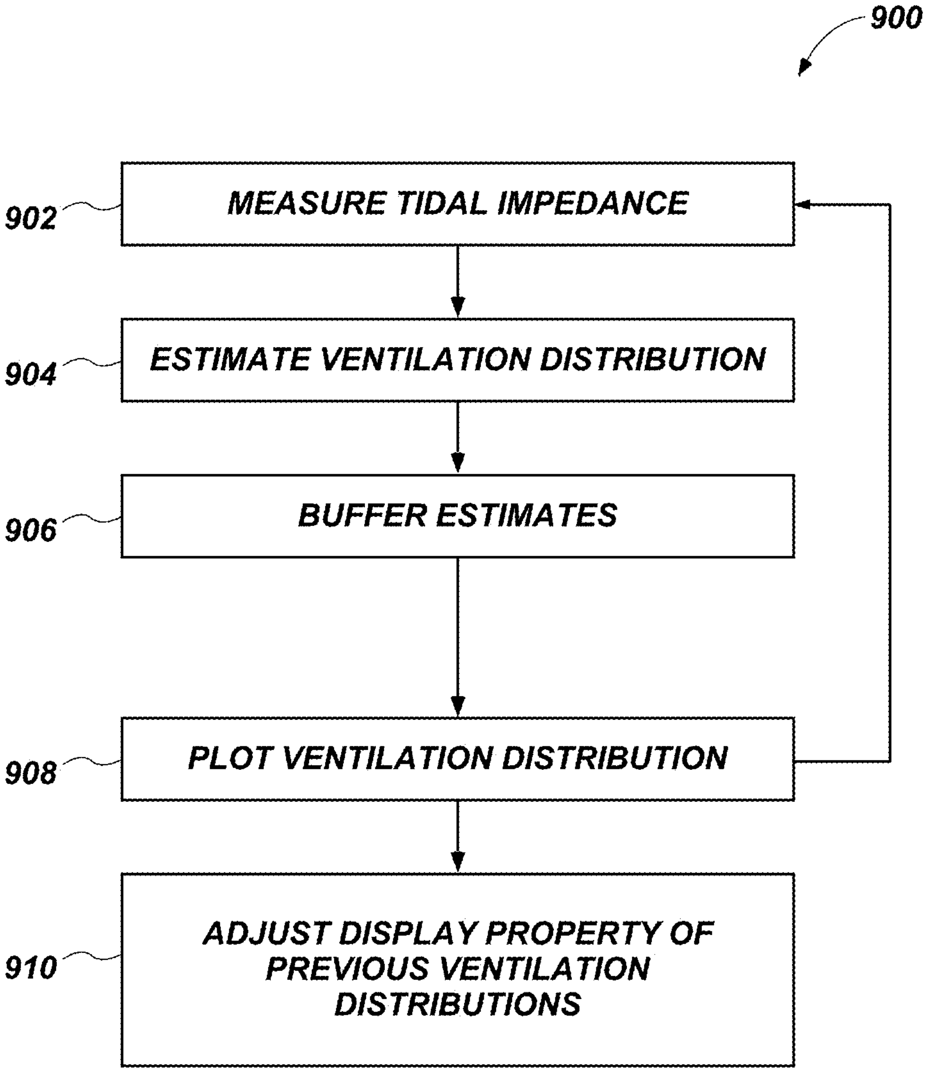
FIG. 9 is a flowchart representing a method of displaying a ventilation distribution of a patient according to an embodiment of the present disclosure.

FIG. 9 illustrates a method of determining, generating, and displaying a graphical representation of a measured ventilation distribution of a patient 900. The method may include measuring the tidal impedance of the lungs of the patient in act 902 of FIG. 8. The tidal impedance of the lungs of the patient may be measured using methods or devices, such as EIT, CT, MRI, ultrasonic flow meters, tracer gas, etc. For instance, the tidal impedance of the lungs may be measure via any of the manners described in U.S. patent application Ser. No. 16/272,600, to Holzhacker, Titled: SYSTEMS AND METHODS TO DETERMINE A PATIENT'S RESPONSIVENESS TO AN ALVEOLAR RECRUITMENT MANEUVER, and published as U.S. Patent Pub. No. 2019/0246949A1, the disclosure of which is incorporated in its entirety by reference herein.

Based on the measure tidal impedance, a distribution measurement of the ventilation distribution measurement of the patient may be determined as shown in act 904 of FIG. 8. Each distribution measurement may include a side-to-side percentage, such as right distribution percent or left distribution percent. In some embodiments, the distribution measurement may further include a front-to-back percentage, such as anterior distribution percent or posterior distribution percent.

In some embodiments, the distribution measurement may recorded in a buffer in act 906. For example, the distribution measurement may be recorded into a circular buffer. The circular buffer may record each distribution measurement until the buffer is full. Once the buffer is full, the next distribution measurement may be recorded over the oldest distribution measurement. In some embodiments, the buffer may be configured to hold between about 20 distribution measurements and about 1,000 distribution measurements, such as between about 50 distribution measurements and about 900 distribution measurements, or between about 100 distribution measurements and about 500 distribution measurements. The number of distribution measurements may be selected based on factors such as display size, estimated frequency, etc. A larger number of distribution measurements may provide more information for the physician. However, as the number of distribution measurements increases the display may also be more difficult to read. Therefore, a size of the buffer may be determined to provide sufficient information without causing the display to be too difficult to interpret. In some embodiments, the distribution measurements may only be buffered for purpose of the display and each of the distribution measurements may be recorded separately, such as in a spreadsheet, table, etc. such that distribution measurements that are no longer being displayed may be accessed when necessary.

Each distribution measurement may then be plotted on a Cartesian coordinate in act 908. The Cartesian coordinate may be arranged such that a horizontal axis corresponds to the side-to-side percentage and a vertical axis corresponds to the front-to-back percentage. For example, an intersection between the vertical axis and the horizontal axis at a central point of the Cartesian coordinate may substantially correspond to a central point in the patient. A left hand side of the patient may correspond to a region of the Cartesian coordinate to the left of the vertical axis and a right hand side of the patient may correspond to a region of the Cartesian coordinate to the right of the vertical axis. An anterior side of patient may correspond to a region of the Cartesian coordinate above the horizontal axis and a posterior side of the patient may correspond to a region of the Cartesian coordinate below the horizontal axis.

After the distribution measurement is plotted in act 908, acts 902 through 906 may be repeated estimating the ventilation distribution of the patient again. In some embodiments, the process may be repeated at specified intervals, such as once a minute, once every thirty seconds, once every two minutes, etc. In some embodiments, the process may be repeated upon the occurrence of an event, such as every time the patient breaths in, every time the patient breaths out, every time the patient breaths in or out, etc.

After each measurement is taken in act 902 and the distribution measurement is calculated and recorded in acts 904 and 906, the distribution measurement may be plotted in act 908. To enable an operator, such as a physician, nurse, technician, etc. to differentiate between each distribution measurement, a display property of the previous distribution measurements may be altered in act 910. For example, a shade of the earlier distribution measurements may be lightened such that earlier distribution measurements are lighter than more recent distribution measurements. In some embodiments, each distribution measurement may be lightened every time a new distribution measurement is plotted, such that the plotted distribution measurements form a gradient progressing from lighter earlier distribution measurement to darker later distribution measurements.

In some embodiments, the shade may be from a first color to a second color, such as from green to blue, yellow to green, blue to red, etc. Thus, the earliest distribution measurement, may remain the first color, and each distribution measurement between the earliest distribution measurement and the most recent distribution measurement may form a gradient from the first color to the second color where the most recent distribution measurement is the second color. As each new distribution measurement is plotted, the most recent distribution measurement may be plotted in the second color, and the color of each of the previous distribution measurements may be adjusted to the appropriate position in the color gradient between the first color and the second color.

In some embodiments, a first color may be used to indicate the most recent distribution measurement and all other distribution measurements may be adjusted to a gradient in another color. For example, the most recent distribution measurement may be displayed in a color such as red, blue, green, etc., and the gradient may be in a less obtrusive color.

In some embodiments, gradient may be adjusted in a manner such that the more recent distribution measurements are more intense (e.g., Contrast between a background of the Cartesian coordinate and the more recent distribution measurements and a lower contrast between the background of the Cartesian coordinate and the older distribution measurements). For example, if the background of the Cartesian coordinate is white, the gradient may progress in the gray scale from black to white where the more recent distribution measurements are near the black end of the gray scale spectrum and the older distribution measurements are near the white end of the gray scale spectrum.

The embodiments of the present disclosure provide a tool that may enable a physician to quickly diagnose a pulmonary condition or ailment in a patient and/or evaluate a treatment. In medical situations a quick diagnosis may be the difference between life and death for the patient. Similarly, quickly identifying an ineffective treatment may enable a physician to alter the treatment before a condition or ailment progresses to a more dangerous condition. Additionally, medical care can be expensive, providing a physician with a tool that may provide for quicker diagnosis and/or treatment may enable the physician to properly treat a patient with less time in the room and potentially enable the patient to leave the medical center earlier both of which may reduce the costs of medical care and enable the physician to treat more patients.

Additional non limiting example embodiments of the disclosure are described below.

Embodiment 1: A method of displaying a ventilation distribution for a patient comprising: obtaining a first ventilation distribution for the patient at a first time; plotting the first ventilation distribution within a graphical user interface of a display; obtaining a second ventilation distribution for the patient at a second time; plotting the second ventilation distribution within the graphical user interface of the display; and in response to plotting the second ventilation distribution, adjusting a visual property of the first ventilation distribution, wherein the adjusted visual property of the first ventilation distribution visually distinguishes the first ventilation distribution from the second ventilation distribution.

Embodiment 2: The method of embodiment 1, wherein the graphical user interface comprises Cartesian coordinates.

Embodiment 3: The method of embodiment 2, wherein an x-axis of the Cartesian coordinates represents a side-to-side distribution of the ventilation distribution.

Embodiment 4. The method of embodiments 2 or 3, wherein a y-axis of the Cartesian coordinates represents a front-to-back distribution of the ventilation distribution.

Embodiment 5: The method of any one of embodiments 1 through 4, further comprising: obtaining a third ventilation distribution for the patient at a third time; plotting the third ventilation distribution on the graphical user interface of the display; and adjusting the visual property of the first ventilation distribution and a visual property of the second ventilation distribution, wherein the adjusted visual property of the first ventilation distribution visually distinguishes the first ventilation distribution from the second ventilation distribution and the third ventilation distribution, and wherein the adjusted visual property of the second ventilation distribution visually distinguishes the second ventilation distribution from the first ventilation distribution and the third ventilation distribution.

Embodiment 6: The method of embodiment 5, wherein adjusting the visual properties of each of the first ventilation distribution and the second ventilation distribution further comprises adjusting the visual properties of each of the first ventilation distribution and the second ventilation distribution such that a gradient of color is represented from the first ventilation distribution to the third ventilation distribution.

Embodiment 7: The method of any one of embodiments 1 through 6, wherein the visual property comprises one or more of a color, a brightness, or a contrast.

Embodiment 8: A system for displaying a ventilation distribution of a patient comprising: a measuring system for measuring the ventilation distribution of the patient; a display device; and a controller operably coupled to the measuring system and the display device, the controller comprising: at least one processor; and at least one non-transitory computer readable storage medium storing instructions thereon that, when executed by the at least one processor, cause the at least one processor to: cause the measuring system to measure the ventilation distribution of the patient at a time interval; and plot an element representing the measured ventilation distribution of the patient within a Cartesian coordinate system of a graphical user interface of the display device, wherein the element is plotted with a higher intensity relative to other elements representing previously measured ventilation distributions of the patient.

Embodiment 9: The system of embodiment 8, wherein the time interval is defined as a time between breathes of the patient.

Embodiment 10: The system of embodiments 8 or 9, wherein the intensity comprises one or more of a color intensity, a brightness, or a contrast.

Embodiment 11: The system of any one of embodiments 8 through 10, wherein a horizontal axis of the Cartesian coordinate system corresponds to a side-to-side ventilation distribution.

Embodiment 12: The system of any one of embodiments 8 through 11, wherein a vertical axis of the Cartesian coordinate system corresponds to a front-to-back ventilation distribution.

Embodiment 13: The system of any one of embodiments 8 through 12, wherein an element representing a most recent measured ventilation distribution of the patient is plotted in a different color than elements representing previously measured ventilation distributions.

Embodiment 14: The system of embodiment 13, wherein the elements representing previously measured ventilation distributions are each plotted in gradients of a second color.

Embodiment 15: The system of embodiment 14, wherein a first gradient of the gradients of the second color forms a first contrast between an element representing an earliest measured ventilation distribution and a background of the Cartesian coordinate that is less than a second contrast formed by a second gradient of the gradients of the second color between an element representing a most-recent previously measured ventilation distribution and the background of the Cartesian coordinate.

Embodiment 16: A system for displaying a ventilation distribution of a patient comprising: at least one processor; and at least one non-transitory computer readable storage medium storing instructions thereon that, when executed by the at least one processor, cause the at least one processor to repeatedly: receive a ventilation distribution measurement of the patient; display the ventilation distribution measurement of the patient; and adjust a visual intensity of one or more earlier displayed ventilation distribution measurement.

Embodiment 17: The system of embodiment 16, wherein the at least one processor receives a ventilation distribution measurement each time the patient breathes in.

Embodiment 18: The system of embodiments 16 or 17, wherein the visual intensity of the one or more earlier ventilation distribution measurements is adjusted such that a more recent ventilation distribution measurement is visually emphasized over an earlier ventilation distribution measurement.

Embodiment 19: The system of any one of embodiments 16 through 18, wherein the visual intensity of the one or more earlier ventilation distribution measurements is adjusted such that a gradient is formed between an earliest ventilation distribution measurement and a most recent ventilation distribution measurement.

Embodiment 20: The system of any one of embodiments 16 through 19, wherein a most recent ventilation distribution measurement is displayed in a first color and the one or more earlier ventilation distribution measurements are displayed in gradients of a second color.

Embodiment 21: A method of displaying a ventilation distribution for a patient comprising: obtaining a first ventilation distribution for the patient at a first time; obtaining a first perfusion distribution for the patient at the first time; plotting the first ventilation distribution within a graphical user interface of a display; plotting the first perfusion distribution within the graphical user interface of the display; obtaining a second ventilation distribution for the patient at a second time; obtaining a second perfusion distribution for the patient at the second time; plotting the second ventilation distribution within the graphical user interface of the display; plotting the second perfusion distribution within the graphical user interface of the display; in response to plotting the second ventilation distribution, adjusting a visual property of the first ventilation distribution, wherein the adjusted visual property of the first ventilation distribution visually distinguishes the first ventilation distribution from the second ventilation distribution; and in response to plotting the second perfusion distribution, adjusting a visual property of the first perfusion distribution, wherein the adjusted visual property of the first perfusion distribution visually distinguishes the first perfusion distribution from the second perfusion distribution.

Embodiment 22: The method of embodiment 21, wherein the first and second ventilation distributions are plotted in shades of a color that are different from a color in which the first and second perfusion distributions are plotted.

Embodiment 23: The method of embodiments 21 or 22, wherein the first and second ventilation distributions are plotted as objects that have a different size from objects with which the first and second perfusion distributions are plotted.

Embodiment 24: The method of any one of embodiments 21 through 23, wherein the first and second ventilation distributions are plotted as objects that have a different shape from objects with which the first and second perfusion distributions are plotted. The embodiments of the disclosure described above and illustrated in the accompanying drawing figures do not limit the scope of the invention, since these embodiments are merely examples of embodiments of the invention, which is defined by the appended claims and their legal equivalents. Any equivalent embodiments are intended to be within the scope of this disclosure. Indeed, various modifications of the present disclosure, in addition to those shown and described herein, such as alternative useful combinations of the elements described, may become apparent to those skilled in the art from the description. Such modifications and embodiments are also intended to fall within the scope of the appended claims and their legal equivalents.

What is claimed is:

1. A method of displaying a ventilation distribution for a patient comprising:

obtaining a first ventilation distribution for the patient during a first time interval, the first ventilation distribution comprising a first data point representative of a left-to-right ventilation distribution along a left-to-right axis in a plane perpendicular to the cranial caudal axis and an anterior-to-posterior ventilation distribution along an axis perpendicular to the left-to-right axis and in the plane perpendicular to the cranial caudal axis;

plotting the first ventilation distribution within a graphical user interface of a display;

obtaining a second ventilation distribution for the patient during a second time interval, the second ventilation distribution comprising a second data point representative of the left-to-right ventilation distribution and the anterior-to-posterior ventilation distribution;

plotting the second ventilation distribution within the graphical user interface of the display; and in response to plotting the second ventilation distribution, adjusting a visual property of the first ventilation distribution, wherein the adjusted visual property of the first ventilation distribution visually distinguishes the first ventilation distribution from the second ventilation distribution.

2. The method of claim 1, wherein the graphical user interface comprises Cartesian coordinates.

3. The method of claim 2, wherein an x-axis of the Cartesian coordinates represents the left-to-right ventilation distribution of the ventilation distribution.

4. The method of claim 2, wherein a y-axis of the Cartesian coordinates represents the anterior-to-posterior ventilation distribution of the ventilation distribution.

5. The method of claim 1, further comprising:

obtaining a third ventilation distribution for the patient during a third time interval, the third ventilation distribution comprising a third data point representative of the left-to-right ventilation distribution and the anterior-to-posterior ventilation distribution;

plotting the third ventilation distribution on the graphical user interface of the display; and adjusting the visual property of the first ventilation distribution and a visual property of the second ventilation distribution, wherein the adjusted visual property of the first ventilation distribution visually distinguishes the first ventilation distribution from the second ventilation distribution and the third ventilation distribution, and wherein the adjusted visual property of the second ventilation distribution visually distinguishes the second ventilation distribution from the first ventilation distribution and the third ventilation distribution.

6. The method of claim 5, wherein adjusting the visual properties of each of the first ventilation distribution and the second ventilation distribution further comprises adjusting the visual properties of each of the first ventilation distribution and the second ventilation distribution such that a gradient of color is represented from the first ventilation distribution to the third ventilation distribution.

7. The method of claim 1, wherein the visual property comprises one or more of a color, a brightness, or a contrast.

8. A system for displaying a ventilation distribution of a patient comprising:

a measuring system for measuring the ventilation distribution of the patient;

a display device;

a controller operably coupled to the measuring system and the display device, the controller comprising:

at least one processor; and at least one non-transitory computer readable storage medium storing instructions thereon that, when executed by the at least one processor, cause the at least one processor to:

cause the measuring system to measure the ventilation distribution of the patient during a time interval, the ventilation distribution comprising a left-to-right ventilation distribution along a left-to-right axis in a plane perpendicular to the cranial caudal axis and an anterior-to-posterior ventilation distribution along an axis perpendicular to the left-to-right axis and in the plane perpendicular to the cranial caudal axis; and plot an element representing the measured ventilation distribution of the patient within a Cartesian coordinate system of a graphical user interface of the display device, wherein the element is plotted with a higher intensity relative to other elements representing previously measured ventilation distributions of the patient, and wherein a visual intensity of the other elements representing previously measured ventilation distributions of the patient is adjusted.

9. The system of claim 8, wherein the time interval is defined as a time between breaths of the patient.

10. The system of claim 8, wherein the intensity comprises one or more of a color intensity, a brightness, or a contrast.

11. The system of claim 8, wherein a horizontal axis of the Cartesian coordinate system corresponds to the left-to-right ventilation distribution.

12. The system of claim 8, wherein a vertical axis of the Cartesian coordinate system corresponds to the anterior-to-posterior ventilation distribution.

13. The system of claim 8, wherein an element representing a most recent measured ventilation distribution of the patient is plotted in a different color than elements representing previously measured ventilation distributions.

14. The system of claim 13, wherein the elements representing previously measured ventilation distributions are each plotted in gradients of a second color.

15. The system of claim 14, wherein a first gradient of the gradients of the second color forms a first contrast between an element representing an earliest measured ventilation distribution and a background of the Cartesian coordinate that is less than a second contrast formed by a second gradient of the gradients of the second color between an element representing a most-recent previously measured ventilation distribution and the background of the Cartesian coordinate.

16. A system for displaying a ventilation distribution of a patient comprising:

at least one processor; and at least one non-transitory computer readable storage medium storing instructions thereon that, when executed by the at least one processor, cause the at least one processor to repeatedly:

receive a ventilation distribution of the patient during a time interval, the ventilation distribution comprising a data point representative of a left-to-right ventilation distribution along a left-to-right axis in a plane perpendicular to the cranial caudal axis and an anterior-to-posterior ventilation distribution along an axis perpendicular to the left-to-right axis and in the plane perpendicular to the cranial caudal axis;

display the ventilation distribution of the patient; and adjust a visual intensity of one or more earlier displayed ventilation distributions.

17. The system of claim 16, wherein the at least one processor receives a ventilation distribution each time the patient breathes in.

18. The system of claim 16, wherein the visual intensity of the one or more earlier ventilation distributions is adjusted such that a more recent ventilation distribution is visually emphasized over an earlier ventilation distribution.

19. The system of claim 16, wherein the visual intensity of the one or more earlier ventilation distributions is adjusted such that a gradient is formed between an earliest ventilation distribution and a most recent ventilation distribution.

20. The system of claim 16, wherein a most recent ventilation distribution is displayed in a first color and the one or more earlier ventilation distributions are displayed in gradients of a second color.

21. A method of displaying a ventilation distribution for a patient comprising:

obtaining a first ventilation distribution for the patient at a first time, the first ventilation distribution comprising a left-to-right ventilation distribution along a left-to-right axis in a plane perpendicular to the cranial caudal axis and an anterior-to-posterior ventilation distribution along an axis perpendicular to the left-to-right axis and in the plane perpendicular to the cranial caudal axis;

obtaining a first perfusion distribution for the patient at the first time;

plotting the first ventilation distribution within a graphical user interface of a display;

plotting the first perfusion distribution within the graphical user interface of the display;

obtaining a second ventilation distribution for the patient at a second time;

obtaining a second perfusion distribution for the patient at the second time;

plotting the second ventilation distribution within the graphical user interface of the display;

plotting the second perfusion distribution within the graphical user interface of the display;

in response to plotting the second ventilation distribution, adjusting a visual property of the first ventilation distribution, wherein the adjusted visual property of the first ventilation distribution visually distinguishes the first ventilation distribution from the second ventilation distribution; and in response to plotting the second perfusion distribution, adjusting a visual property of the first perfusion distribution, wherein the adjusted visual property of the first perfusion distribution visually distinguishes the first perfusion distribution from the second perfusion distribution.

22. The method of claim 21, wherein the first and second ventilation distributions are plotted in shades of a color that are different from a color in which the first and second perfusion distributions are plotted.

23. The method of claim 21, wherein the first and second ventilation distributions are plotted as objects that have a different size from objects with which the first and second perfusion distributions are plotted.

24. The method of claim 21, wherein the first and second ventilation distributions are plotted as objects that have a different shape from objects with which the first and second perfusion distributions are plotted.

* * * * *